United States Patent [19]

Ko

[11] 4,044,121

[45] Aug. 23, 1977

[54] HAIR SPRAY CONTAINING FLUOROCARBON COMPOUNDS AS ADDITIVES

[75] Inventor: Su Sen Ko, Shoreview, Minn.

[73] Assignee: Minnesota Mining and Manufacturing Company, Saint Paul, Minn.

[21] Appl. No.: 665,922

[22] Filed: Mar. 11, 1976

[51] Int. Cl.$^2$ .............................................. A61K 7/11
[52] U.S. Cl. ........................................ 424/71; 8/127.51; 132/7; 424/DIG. 1; 424/DIG. 2; 424/47
[58] Field of Search ................ 424/DIG. 1, DIG. 2, 424/47, 71; 8/127.51; 132/7

[56] References Cited

U.S. PATENT DOCUMENTS

| 3,171,784 | 3/1965 | Witiver ................................. 424/47 |
| 3,959,462 | 5/1976 | Parks et al. ........................... 424/70 |
| 3,972,998 | 8/1976 | Keiner ................................... 424/70 |
| 3,993,745 | 11/1976 | Cella et al. ........................... 424/71 |
| B 464,491 | 3/1976 | Pavlik et al. ...................... 424/71 X |

*Primary Examiner*—Albert T. Meyers
*Assistant Examiner*—Vera C. Clarke
*Attorney, Agent, or Firm*—Cruzan Alexander; Donald M. Sell; Carolyn A. Bates

[57] ABSTRACT

Hair spray compositions are disclosed comprising conventional film-forming resins in a solvent vehicle to which have been added fluorocarbon compounds formed by the reaction of an aromatic anhydride or dibasic acid and a fluorocarbon amine or alcohol.

14 Claims, No Drawings

HAIR SPRAY CONTAINING FLUOROCARBON COMPOUNDS AS ADDITIVES

BACKGROUND OF THE INVENTION

1. Field of the Invention

This invention relates to hair spray compositions and a method of treating hair. More specifically, it relates to hair spray compositions containing fluorocarbon additives and conventional film-forming resins.

2. Description of the Prior Art

In today's society a great deal of attention is paid to personal appearance. Of particular concern to most people is the neatness and attractive appearance of their hair. Considerable time and money is spent curling hair and arranging it into attractive styles. However, the hair often loses its curl and style as a result of exposure to wind and weather or by mechanical agitation.

To alleviate this problem, hair sprays have been developed which are uniformly deposited on the hair to maintain curl and style for longer periods of time. These hair sprays typically contain a film-forming resin, a solvent, and miscellaneous additives such as plasticizers and perfumes. When these hair spray compositions are applied to the hair, the solvent evaporates and a film of the resin is left on the hair to hold the hair in place.

A variety of film-forming resins have been used in hair spray compositions. These range from the softer vinylpyrrolidone polymers and copolymers thereof to the somewhat harder esters of maleic anhydride methylvinyl ether copolymers.

A major problem with conventional film-forming resins used in hair sprays is their sensitivity to moisture and humidity. Thus, upon exposure to rain or humidity, the resin loses some of its ability to maintain the hair style.

To improve the humidity resistance of film-forming resins, fluoroorganic radicals have been previously employed. German Offenleggunsscrift 2,314,659 discloses copolymers of vinyl esters, unsaturated acids and co-polymerizable fluorocarbon compounds as hair-treating compositions. Cosmetic preparations to shorten hair drying time comprising fluorochemical acrylate polymers or copolymers are disclosed in British Pat. No. 1,268,636 and Canadian Pat. No. 940,049. British Pat. No. 1,290,367 discloses film-forming polar polymers containing 0.5 to 15 percent fluorine and 5 to 22 percent pendent carboxyl groups and hairstyling compositions containing them. These foreign patents relate, in general, to fluorine-modified polymers in hair-treating compositions, and do not describe the simple addition of small amounts of non-polymeric fluorochemicals to hair spray compositions containing nonfluorinated film-forming resins.

British Pat. No. 1,312,675 and French Pat. No. 2,054,478 describe the use of monomeric and polymeric fluorochemicals in a method of treating hair, either by themselves or mixed with one or more other materials. These patents do not utilize fluorocarbon compounds as simple additives to hair spray compositions containing conventional film-forming resins. Rather, the fluorocarbon compound itself is the major hair treating ingredient of the compositions described therein. Additionally, the fluorocarbon compounds utilized in these prior art compositions do not contain an aromatic non-fluorinated moiety.

A recent commercial hair spray product sold in the United States under the trademark "ALBERTO VO₅" by Alberto Culver Company contains a film-forming resin which is believed to be a half ester of methylvinyl ether maleic anhydride copolymer, and this product also contains a fluorocarbon ingredient. Although the exact nature of this fluorocarbon ingredient is not known, it is presently believed to contain phosphorus. This ingredient is distinguishable from the fluorocarbon additives of the present invention both in chemical structure and in performance on human hair.

The improved hair spray compositions of the present invention provide significant advantages over hair sprays of the prior art. The present compositions impart superior soil resistance to the hair, and curl retention following momentary immersion in water is particularly improved. The present compositions are resistant to high humidity, nontacky and readily removed from the hair by shampooing. The toxicity of the compositions, as measured by the degree of eye irritation, is very low. Additionally, the fluorocarbon additives of the present invention are effective in very low concentrations, thereby offering significant economic advantages. Since there is no chemical interaction between the film-forming resin and the fluorocarbon additive, a wide range of combinations of ingredients is possible. Other advantages of the present invention will be apparent from a further description of the invention herein below.

BRIEF DESCRIPTION OF THE INVENTION

The present invention provides novel compositions and a method for treating hair to enable the hair to retain its style despite exposure to wind, humidity, moisture and physical agitation.

In accordance with the present invention, improved hair spray compositions are provided which comprise conventional, non-fluorinated, film-forming resins and a fluorochemical additive compatible therewith. The film-forming resins and the fluorochemical additives are dissolved and/or dispersed in a suitable liquid solvent vehicle such as ethanol, and the compositions may optionally contain plasticizers, perfumes, etc., conventionally used in hair spray compositions. If the composition is applied as an aerosol, conventional propellants may also be present.

The essence of the invention resides in the particular fluorochemical additives, in combination with conventional non-fluorinated film-forming resins, which provide the improved properties of the hair spray compositions.

DETAILED DESCRIPTION

The fluorochemical additives that are useful in the present invention are vehicle soluble, dermally nonirritating compounds represented by the formula:

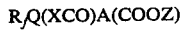

R$_f$Q(XCO)A(COOZ)    Formula I wherein
R$_f$ is a monovalent, fluorinated, saturated, aliphatic radical having 3 to 20 carbon atoms, and at least one terminal perfluorinated carbon atom;
Q is a divalent linking group;
X is —O— or —NR— where R is hydrogen or alkyl having 1 to 14 carbon atoms;
A is phenylene containing only hydrogen substituents on the aromatic carbon atoms, or phenylene wherein one or more of said hydrogens have been replaced by chlorine, bromine, alkyl having 1 to 4 carbon atoms, nitro, alkoxy having 1 to 4 carbon atoms, or combinations thereof;

Z is hydrogen or a cation selected from the group consisting of $NH_4^+$, $Na^+$, $K^+$, $Li^+$, a protonated alkyl amine or alkanol amine having 1 to 6 carbon atoms, and quaternized forms of said amines.

The term "vehicle soluble" as used herein refers to the property of being soluble or dispersible in the solvent vehicle used in the composition. Generally, this vehicle is non-toxic, low boiling alcohol such as ethanol or isopropanol, and non-aerosol compositions may contain some water.

The term "dermally non-irritating" as used herein refers to the lack of adverse reaction by skin or eyes when the compositions are applied to human hair.

The carbon atoms of the $R_f$ moiety of Formula I are preferably substituted only by fluorine, chlorine or hydrogen with no more than one hydrogen or chlorine atom for every two carbon atoms, and the terminal carbon atom (the carbon atom furthermost from the open valence) is perfluorinated. Most preferred is a perfluorinated carbon radical, however, a divalent oxygen or trivalent nitrogen atom bonded only to carbon atoms, can be present in the skeletal chain. $R_f$ moieties containing 4 to 12 carbon atoms in the skeletal chain are preferred, and most preferred are $R_f$ moieties containing 8 perfluorinated carbon atoms.

The divalent linking group "Q" of Formula I has a valency of two and may vary greatly in structure. Its primary function is to link the $R_f$ moiety to the rest of the molecule. The "Q" linking group must be free of reactive groups which chemically interfere with the formation of the ester or amide linkage "(XCO)", and does not contain heteroatoms other than sulfur, oxygen or nitrogen. The "Q" group is preferably selected from the group consisting of: alkylene [—$(CH_2)_n$—], sulfonamido alkylene [—$SO_2NR(CH_2)_n$—], alkylene carboxyloxy alkylene [—$(CH_2)_nCOOCH_2CH_2$—], sulfonamido alkyleneoxy alkylene [—$SO_2NR(CH_2CH_2O)_nCH_2CH_2$—, sulfonato phenylene

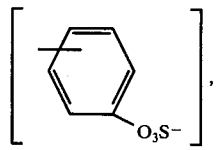

and sulfonamido phenylene

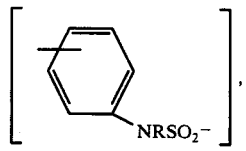

where "R" is hydrogen or alkyl having 1 to 14 carbon atoms and "N" is an integer from 1 to 15.

The "A" portion of Formula I is a phenylene

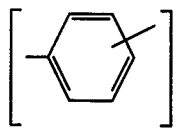

radical wherein all of the aromatic carbon atoms are substituted by hydrogen, or where one or more of the hydrogen atoms attached to aromatic carbon atoms have been replaced by chlorine, bromine, alkyl or alkoxy groups having 1 to 4 carbon atoms, or nitro. The "A" portion of the molecule is derived from dibasic acids or anhydrides which are commercially available or readily prepared by conventional methods. "A" groups derived from starting materials which are difficult to prepare due to steric hindrance such as phenylene compounds containing adjacent t-butyl or isopropyl substitutions are not contemplated within the scope of the invention.

The fluorocarbon compounds of Formula I are useful in the present invention and may be prepared in a variety of ways known in the art. Most conveniently, the compounds are prepared by reacting a precursor fluorochemical amine or alcohol with a suitable precursor anhydride or dibasic acid. Precursor amines and alcohols will have the structure $R_fQXH$ where "$R_f$", "Q" and "X" are as described above. Useful illustrative examples of such precursor amines and alcohols include:

$CF_3(CF_2)_3SO_2N(CH_2CH_3)CH_2CH_2OH$
$CH_3(CF_2)_3SO_2N(CH_3)CH(CH_3)CH_2OH$
$CF_3(CF_2)_3SO_2N(CH_3)CH_2CH(CH_3)OH$
$C_6F_{13}SO_2NCH_3(CH_2)_4OH$
$CF_3(CF_2)_6SO_2CH_2CH_2OH$
$CH_3(CF_2)_6COCH_2CH_2OH$
$C_7F_{15}CON(C_2H_5)C_2H_4OH$
$C_7F_{15}CON(CH_3)CH_2CH_2OH$
$CF_3(CF_2)_7SO_2N(CH_3)CH_2CH_2OH$
$CF_3(CF_2)_7SO_2N(CH_2CH_3)CH_2CH_2OH$
$CF_3(CF_2)_9SO_2N(CH_2CH_2CH_3)CH_2CH_2OH$
$CF_3(CF_3)_7SO_2N(CH_2CH_2CH_3)CH_2CH_2OH$
$CF_3(CF_2)_7SO_2N(C_2H_5)(CH_2)_6OH$
$CF_3(CF_2)_7SO_2N(C_2H_5)(CH_2)_{11}OH$
$CF_3(CF_2)_7SO_2N(C_4H_9)(CH_2)_4OH$
$CF_3(CF_2)_7SO_2N(CH_3)(CH_2)_4OH$
$C_8F_{17}SO_2N(C_4H_9)CH_2CH_2OH$
$C_8F_{17}SO_2N(CH_3)(CH_2)_4OH$
$C_8F_{17}SO_2N(CH_3)(CH_2)_{11}OH$
$CF_3(CF_2)_7SO_2N(C_3H_7)CH_2OCH_2CH_2CH_2OH$
$C_2F_5O(C_2F_4O)_3CF_2CONHC_2H_4OH$

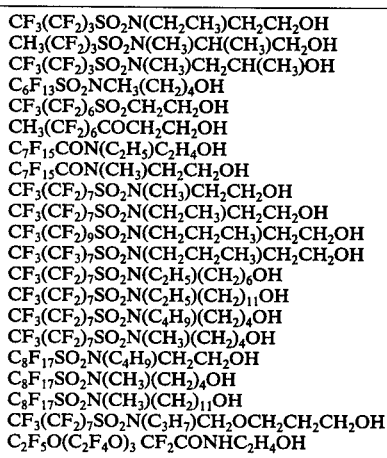

$C_7F_{15}CH_2NH_2$
$C_8F_{17}SO_2N(C_2H_5)CH_2CH_2NHCH_2CH_2NH_2$
$C_8F_{17}SO_2N(C_2H_5)CH_2CONHCH_2CH_2NH_2$
$C_8F_{17}SO_2N(C_4H_9)CH_2CH_2NH_2$
$CF_3(CF_2)_7SO_2N(CH_2CH_3)CH_2CH_2NH_2$

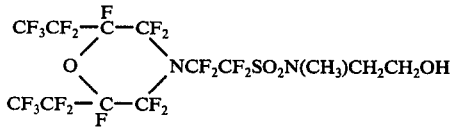

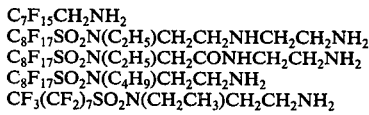

$[CF_3(CF_2)_7SO_2N(CH_2CH_3)CH_2CH_2]_2NH$ and
$CF_3(CF_2)_7SO_2N(CH 2CH_3)CH_2CH_2N(CH_3)H$.

The presently preferred precursor amine and alcohol are

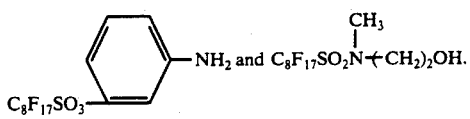 and 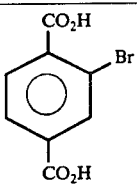
Many of the fluorocarbon alcohols and amines listed above are commercially available and most have been previously described in U.S. Pat. Nos. 3,398,182 and 3,575,897 and British Pat. No. 2,290,367.
Illustrative examples of useful anhydride and dibasic acid starting material are as follows:
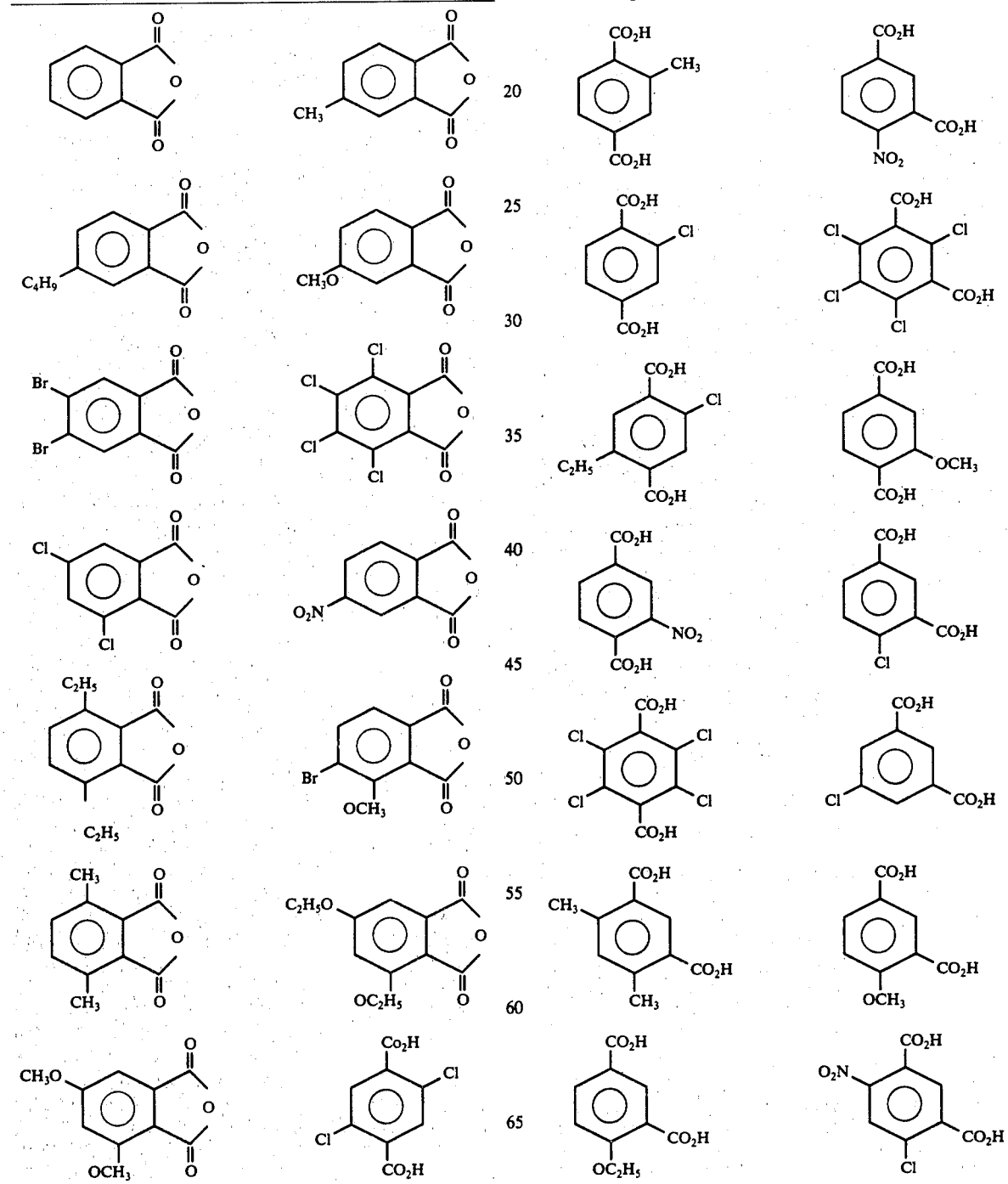

-continued

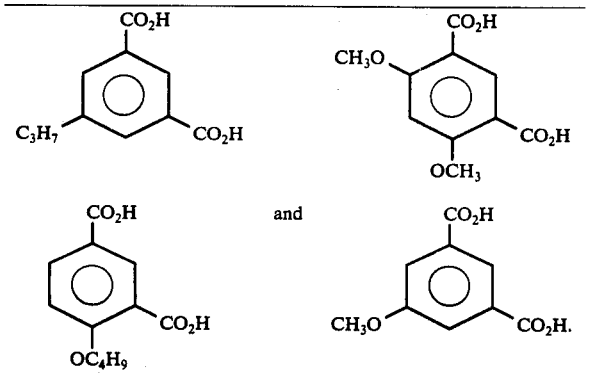

The presently preferred anhydrides are:

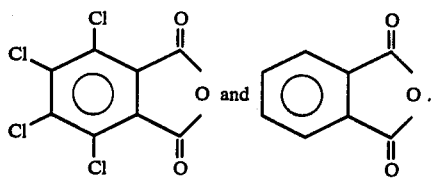

In the reaction which produces the preferred fluorochemical additives of the compositions of the invention, the precursor fluorochemical amine or alcohol is reacted usually with about an equivalent amount of the anhydride. The reaction is most conveniently accomplished in a solvent for both the reactants and the reaction product. Typical solvents for the precursor fluorochemical amine are water miscible and include dimethyl formamide, dimethyl acetamide and N-methyl pyrrolidone, ketones such as acetone or methyl ethyl ketone, ethers such as tetrahydrofuran, and alkoxy ethanols such as 2-ethoxy ethanol or 2-butoxy ethanol (e.g., "Butyl Cellosolve"). Preferred solvents for the precursor alcohols are aprotic and include dimethyl formamide, dimethyl acetamide, N-methyl pyrrolidone, pyridine and triethylamine.

When the precursor alcohol or amine is dissolved in an aprotic solvent, a minimum amount thereof to dissolve the reactants is used, since these solvents are generally removed before the reaction product is added to the hair spray composition.

The dissolved precursor fluorochemical amine is typically reacted with the anhydride by slowly adding the latter to a solution of the former with sufficient agitation to obtain uniform dispersal. Reaction times are relatively short and the reactions are typically carried out at temperatures in the range of about 20° C. - 80° C. and at atmospheric pressures. An ambient (air) reaction atmosphere may be used, but dry nitrogen is preferred.

It has been found that if the reaction temperatures are maintained between about room temperature (20° C.) and 80° C., a high yield of the desired organic fluorochemical compound is produced with minimal side products from secondary reactions. If the temperature is elevated above 85° C., some reaction of the anhydride and solvent may occur or the amide may partly cyclize, reducing the water solubility of the resultant compounds which may be undesirable in some instances.

Fluorochemical alcohols may be reacted with the anhydride by direct melt esterification or in the presence of aprotic solvents, preferably with esterification-promoting catalysts such as perfluoromethane sulfonic acid or a tertiary amine.

Once the reaction has been completed to produce the desired fluorochemical compound, the product may be removed from the reaction solvent, for example, by precipitating it with an aqueous acid solution.

The resultant fluorochemical compound product, which has a free carboxylic acid group, may be neutralized with a slight excess of a base to make it water-soluble or water-dispersible. Suitable bases for this purpose are at least moderately water-soluble and include ammonia, potassium hydroxide, sodium hydroxide, morpholine or an alkylamine, isobutylamine, butylamine, ethanolamine, diethanolamine, diethylaminoethanol, 2-amino-2-ethyl propanol, etc.

According to the invention, at least one fluorocarbon compound of Formula I is added to a composition comprising a conventional film-forming resin dissolved or dispersed in a suitable vehicle, typical ethanol or isopropanol. The term "film-forming resin" refers to a polymer which is used as a hair fixative. The requisite properties of film-forming resins used in hair preparations are well known in the art. The resin must be water-soluble or at least swellable in water so that it can be readily removed by shampooing. The resin must be soluble in the solvent vehicle used, which is normally ethanol or isopropanol, and it must be compatible with the propellent used if an aerosol preparation is desired. When sprayed on the hair, the resin should dry to a clear and glossy film which is flexible enough to allow combing, yet it must adhere to the hair strands well enough to hold the hair style for a suitable length of time. The resin must also be non-toxic to skin and eyes.

One skilled in the art is able to select a proper film-forming resin for use in hair preparations by following the criteria established by McFarland and Scott in Drug and Cosmetic Industry, 98, p. 41, 1966. The major criteria established by these authors include:
1. Hardness — 50 to 60 percent of plate glass,
2. Clarity — transparent,
3. Curl Retention
   — 80 to 90 percent at 50 percent relative humidity and 70° F.
   — 30 to 40 percent at 70 percent relative humidity and 70° F.
   — 30 to 40 percent at 85 percent relative humidity and 70° F.

Among the presently preferred film-forming resins for use according to the present invention are polyvinylpyrrolidone (PVP), (available commercially as PVP K-30 from GAF Corporation), quaternized copolymers of vinyl pyrrolidone (commercially available as Gafquat 734 from GAF Corporation), and the butyl half ester of maleic anhydride, methylvinyl ether copolymer (commercially available as Gantrez ES-425 from GAF Corporation).

An effective amount of fluorochemical additive of Formula I is added to the resin solution. The fluorocarbon should constitute between 0.005 and 5.0 percent by weight of the hair spray composition. The film-forming resin preferably ranges from 1 to 7 percent by weight of the composition. The amount of fluorocarbon additive is preferably less than the amount of resin. The remainder of the composition is primarily a solvent which is preferably a non-toxic, low boiling point alcohol, such as ethanol or isopropanol, although some water may be present. Minor proportions of other ingredients such as neutralizers, plasticizers, perfumes, protein, etc., are conventionally used in such compositions.

If an aerosol preparation is desired, propellents such as carbon dioxide, "Freons" and isobutane may be added to the composition as is well known in the art.

The improved hair spray compositions of the invention are used in the conventional manner by applying a uniform mist to dry, styled hair, and the solvent allowed to evaporate. The compositions are particularly effective in imparting dry soil resistance to treated hair and in protecting treated hair from the effects of humidity and moisture.

Compositions according to the invention were applied to tresses of human hair, and the treated hair was evaluated according to the following test procedures

Soil Resistance Test

This test measures the ability of the test composition to prevent dirt pick-up by treated hair.

According to the test procedure, bleached white human hair tresses approximately 15 cm. long (two grams) were sprayed 20 times with the test composition using a Mark I spray pump (Calmar Pumps, Division of Diamond Inernational). The treated tresses were dried for 0.5 to 1 hour at 60° C. Initial reflectance readings ($L_o$) were taken at three different locations on each tress using a Hunter Lab Model D25D Color Difference Meter and the readings were averaged. The individual tresses were then placed in carbons containing 10 grams of dry dirt, and the cartons were shaken 10 times. The hair tresses were removed from the carton, tapped 20 times and combined through 5 times. Readings were taken at three different locations on each tress as before and averaged (L). The percent of dirt pick-up on each tress is expressed as Lo-L/Lo × 100 and the soil resistance value is determined by subtracting this value from 100.

Curl Retention Test

This test measures the ability of the test composition to hold a curl at high relative humidity conditions.

According to the test procedure, 10 tresses of natural brown human hair, each approximately 15 cm. long (two grams) were shampooed twice with a shampoo containing the following ingredients:

| Ingredient | Percent Active | Weight Percent |
| --- | --- | --- |
| Fatty acid alkanolamide | 100 | 37.5 |
| Sodium lauryl sulfate | 28 | 23.5 |
| Sodium coconut ether sulfate | 60 | 18.8 |
| Propylene glycol | | 10.0 |
| Cocoamido alkylbetaine | 30 | 10.0 |
| Perfume | | 0.2 |
| H$_2$O | | Q.S. to 100% |
| Citric acid | | .98 |

The above concentrate has a pH of 8 and is diluted with seven volumes of tap water before use.

The clean tresses were set on smooth plastic rollers approximately 2.53 cm. in diameter, secured with hair clips, and dried in an oven at 60° C. for 3 hours. The tresses were removed from the rollers, brushed five times with a nylon hair brush and recurled with the fingers. Each tress was sprayed five times with the test composition using a Mark I pump. The treated tresses were dried for 0.5 hour at 60° C. and the initial length of the curl ($L_i$) of each tress was measured.

The tresses were then placed in a constant humidity chamber having a relative humidity of 85 to 95 percent. The length of each curl was measured after one hour ($L_1$), three hours ($L_3$) and 24 hours ($L_{24}$) of exposure to this high humidity. The curl retention (C.R.) value for the test composition was determined by averaging the individual values of each of the ten tresses. The value for each tress for each time period ($L_t$) was calculated as follows:

$$\text{Curl Retention (C.R.)} = \frac{15 - L_t}{15 - L_i} \times 100$$

Water Dip Test

This test measures the ability of the test composition to resist curl drop caused by incidental exposure to water.

According to the test procedure, tresses of natural brown hair approximately 15 cm. long (two grams) were shampooed twice with the shampoo described in the curl retention test above. The clean tresses were set on smooth plastic rollers approximately 2.53 cm. in diameter, secured with hair clips and dried in an oven at 60° C. for three hours. The tresses were removed from the rollers, brushed five times with a nylon hair brush and recurled with the fingers. Each tress was sprayed 20 times with the test composition using a Mark I pump. The treated tresses were dried at 60° C. for 0.5 to 1.0 hour, and the initial length of the curl ($L_i$) of each tress was measured. Each tress was then dipped for two seconds in water at a temperature of 24° C. The curl length of each tress was measured at 1 minute ($L_1$), 5 minutes ($L_5$) and 10 minutes ($L_{10}$) after removal from the water. The water dip (W.D.) value for each tress was calculated as follows for each time period:

$$\text{Water Dip (W.D.)} = \frac{15 - L_t}{15 - L_i} \times 100$$

The following examples illustrate representative compositions of the invention and the results of their evaluation in the test methods described above.

The materials used in the examples and designated by tradenames are described below:

1. PVP K-30 — This material is available from GAF Corporation, Chemical Division, 140 West 51st Street, New York, New York 10020. It is described as a vinylpyrrolidone polymer having an average molecular weight of 40,000 and the repeating unit

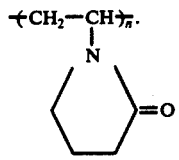

2. Gafquat 734 — This material is available from GAF Corporation at the above address. It is described as a cationically modified vinylpyrrolidione copolymer with molecular weight less than 100,000.

3. Gantrez ES-425 — This material is available from GAF Corporation at the above address. It is described as the butyl half ester of a copolymer of maleic anhydride and methylvinyl ether and has the repeating unit;

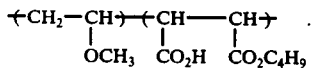

4. Solulan 97 — This material is available from Amerchol, CPC International Incorporated, Amerchol Park, Edison, New Jersey 08817. It is described as an acetylated polyoxyethylene derivative of lanolin (9 moles of ethylene oxide).

5. RD-5179 Perfume — This material is available from Roure Bertrand Dupont, 540 Frontage Road, Northfield, Illinois 60093.

until the salt was completely dissolved. The pH of the composition was adjusted to 6.8 to 6.95 by the addition of AMP. The composition was placed in a pump aerosol dispenser for subsequent evaluation.

The composition was evaluated on human hair in the soil resistance, curl retention and water dip tests described above. The results are summarized in the following table along with other compositions prepared according to the general procedure of this example and designated Examples 2-15. For purposes of comparison with compositions of the present invention, Examples 16 and 17 have been included in the table. These examples are commercially available products.

TABLE I
HAIR SPRAY COMPOSITIONS[1]

| EXAMPLE NUMBER | RESIN | AMOUNT(g) | FLUORO-CHEMICAL | AMOUNT(g) | CURL RETENTION[2] | WATER DIP (1 MIN.) | SOIL RESISTANCE |
|---|---|---|---|---|---|---|---|
| 1 | Gantrez ES-425 | 5.5 | I | 0.5 | 66.8 | 94 | 83 |
| 2 | PVP K-30 | 5.5 | None | — | 59.5 | 4 | 46 |
| 3 | PVP K-30 | 5.5 | I | 0.5 | 61.6 | 83 | 63 |
| 4 | Gafquat 734 | 5.5 | None | — | 45.7 | 76 | 34 |
| 5 | Gafquat 734 | 5.5 | I | 0.5 | — | 93 | 62 |
| 6 | Gantrez ES-425 | 5.5 | None | — | 77.0 | 41 | 64 |
| 7 | Gantrez ES-425 | 5.5 | I | 0.005 | 74.8 | 98 | 68 |
| 8 | Gantrez ES-425 | 5.5 | I | 0.05 | 78.6 | 98 | 66 |
| 9 | Gantrez ES-425 | 5.5 | I | 5.0 | — | 98 | 95 |
| 10 | Gantrez ES-425 | 5.5 | II | 0.005 | 82.6 | 77 | 51 |
| 11 | Gantrez ES-425 | 5.5 | II | 0.05 | 85.8 | 67 | 78 |
| 12 | Gantrez ES-425 | 5.5 | II | 0.5 | 81.3 | 96 | 71 |
| 13 | Gantrez ES-425 | 3.0 | I | 0.5 | — | 86 | 63 |
| 14 | None | — | None | — | — | 50 | 32 |
| 15 | Gantrez ES-425 | 1.9 | I | 0.5 | 91.7[4] | 99[5] | 71[5] |
| 16 | Alberto VO$_5$ with Veron | (3% solids) | | | | 72 | 40 | 68 |
| 17 | Final Net | (6.2% solids) | | | | 67 | 35 | 52 |

[1]Solvent: 8.8 g. of deionized water, q.s. to 100 g. with 95% ethanol; pH adjusted to 6.5–7.0 with AMP.

[2]C.R. = $\dfrac{3\,(24\text{ hr. reading}) + 2\,(3\text{ hr. reading}) + 1\text{ hr. reading}}{6}$

[3]Aerosol formulation - propellant: carbon dioxide (4.6%) methylene chloride (14%). No water was added.
[4]Sprayed 2.5 seconds.
[5]Sprayed 5 seconds.
[6]Alberto Culver Co.
[7]Clairol Incorporated The fluorochemical additive used in the examples was either:
Fluorochemical I:

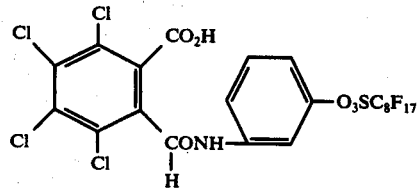

or Fluorochemical II:

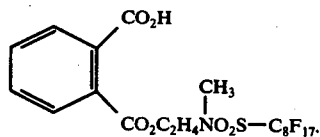

EXAMPLE 1

Eleven grams of Gantrez ES-425 (50% solution in ethanol) and 0.1067 gram of 2-amino-2-methyl-1-propanol (AMP) was added to 84.49 grams of 95 percent ethyl alcohol. The mixture was stirred until it was homogeneous. One-half gram of Solulan 97 (plasticizer), 8.18 grams of deionized water, and 0.1 gram of RD-5179 Perfume, were added sequentially to the mixture. One-half gram of fluorochemical I as the potassium salt was then added, and the mixture was stirred The above data indicate that the incorporation of small amounts of fluorinated organic compounds of the type described herein into hair-setting compositions containing conventional film-forming resins increases the resultant film's resistance to water penetration as evidenced by the higher water dip values for the hair tresses treated with the compositions of the present invention versus those compositions not containing the fluorochemical additive. The compositions of the present invention also increase the hair's resistance to soil when compared to compositions without fluorochemical additives.

The level of the fluorinated compound which is incorporated into the compositions controls the characteristics of the hair-setting compositions with respect to soil resistance and water dip test. While as little as 0.005% by weight of the fluorochemical produces a noticeable improvement over the flim-forming resin without the fluorochemical, 0.5% is generally the preferred level for satisfactory performance. Beyond 0.5% by weight of fluorochemical, only a slight improvmenet is achieved. At the higher percentage levels (e.g., greater than 5.0%), the insolubility of the fluorochemical may become a problem and the compositions also become more expensive to make.

The data also indicate that the overall performance of compositions of the present invention in the tests employed is significantly better than that of currently available, representative commercial hair sprays.

What is claimed is:

1. In a hair spray composition comprising a non-fluorinated film-forming resin in a solvent vehicle, the improvement comprising the addition to said composition of 0.005 to 5.0 percent by weight of said composition of a vehicle-soluble, dermally non-irritating compound of the formula:

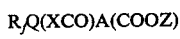

wherein $R_f$ is a monovalent, fluorinated, saturated, aliphatic radical having 3 to 20 carbon atoms and at least one terminal perfluorinated carbon atoms;

Q is a divalent linking group free of reactive groups which would chemically interfere with the formation of ester or amide linkages and free of heteroatoms other than sulfur, oxygen or nitrogen;

X is —O— or —NR— where R is hydrogen or alkyl having 1 to 14 carbon atoms;

A is phenylene containing only hydrogen substituents on the aromatic carbon atoms, or phenylene where one or more of said hydrogen substituents have been replaced by bromine, chlorine, alkyl having 1 to 4 carbon atoms, nitro, alkoxy having 1 to 4 carbon atoms, or combinations thereof;

Z is hydrogen or a cation selected from the group consisting of $NH_4^+$, $Na^+$, $K^+$, $Li^+$, a protonated alkyl amine, a protonated alkanol amine having 1 to 6 carbon atoms and quaternized forms of said amines 2. The composition according to claim 1 wherein the solvent vehicle is ethyl alcohol.

3. The composition according to claim 2 wherein the film-forming resin is polyvinylpyrrolidone.

4. The composition according to claim 2 wherein the film-forming resin is the ethyl or butyl half ester of maleic anhydride methylvinyl ether copolymer.

5. The composition according to claim 1 wherein Q is selected from the group consisting of: $-(CH_2)_n-$, $-SO_2NR(CH_2)_n-$, $-(CH_2)_nCOOCH_2CH_2-$, $-SO_2NR(CH_2CH_2O)_n-$

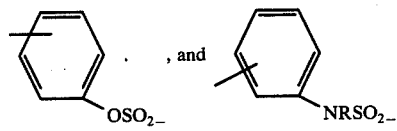

where R is hydrogen or alkyl having 1 to 14 carbon atoms and n is an integer from 1 to 15.

6. The composition according to claim 5 wherein the carbon atoms of the $R_f$ moiety are substituted only by fluorine, chlorine or hydrogen atoms with no more than one hydrogen or chlorine atom for every two carbon atoms, and the skeletal chain may contain a divalent oxygen or trivalent nitrogen atom, bonded only to carbon atoms.

7. The composition according to claim 6 wherein $R_f$ is a perfluorocarbon radical having 4 to 12 carbon atoms.

8. The composition according to claim 7 wherein $R_f$ is $-C_8F_{17}$.

9. The composition according to claim 8 wherein the compound is

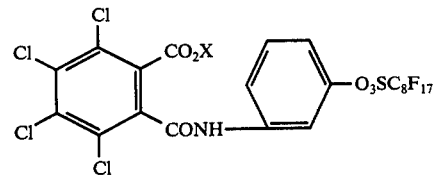

wherein X is H or $K^+$

10. The composition according to claim 8 wherein the compound is:

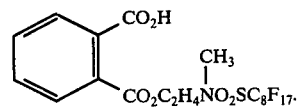

11. In a method of treating human hair comprising applying to the hair an effective amount of a hair spray composition comprising a non-fluorinated film-forming resin in a solvent vehicle, the improvement comprising the addition to said composition of 0.005 to 5.0 percent by weight of said composition of a vehicle-soluble, dermally non-irritating compound of the formula:

wherein $R_f$ is a monovlent, fluorinated, saturated, aliphatic radical having 3 to 20 carbon atoms and at least one terminal perfluorinated carbon atom;

Q is a divalent linking group free of reactive groups which would chemically interfere with the formation of ester or amide linkages and free of heteroatoms other than sulfur, oxygen or nitrogen;

X is —O— or —NR— where R is hydrogen or alkyl having 1 to 14 carbon atoms;

A is phenylene containing only hydrogen substituents on the aromatic carbon atoms or phenylene where one or more of said hydrogen substituents have been replaced by bromine, chlorine alkyl having 1 to 4 carbon atoms, nitro, alkoxy having 1 to 4 carbon atoms, or combinations thereof;

is hydrogen or a cation selected from the group consisting of $NH_4^+$, $Li^+$, a protonated alkanol amine having 1 to 6 carbon atoms and quaternized forms of said amines.

12. The method of claim 11 wherein the solvent vehicle is ethyl alcohol.

13. The method of claim 12 wherein the film-forming resin is the ethyl or butyl half ester of maleic anhydride methylvinyl ether copolymer.

14. The method of claim 13 wherein the compound is:

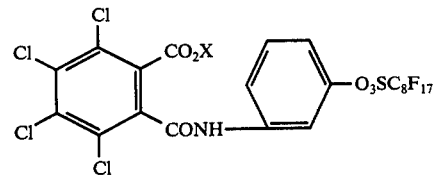

where X is hydrogen or $K^{30}$.

* * * * *

UNITED STATES PATENT AND TRADEMARK OFFICE
CERTIFICATE OF CORRECTION

PATENT NO. : 4,044,121
DATED : August 23, 1977
INVENTOR(S) : SU-SEN KO

It is certified that error appears in the above-identified patent and that said Letters Patent are hereby corrected as shown below:

Col. 3, line 40, change "$_2-$" to -- $_2-1$, --.

Col. 4, line 65, change "$CF_3(CF_2)_7SO_2N(CH2$" to
-- $CF_3(CF_2)_7SO_2N(CH_2$ --.

Col. 6, line 57, change " 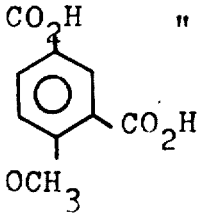 " to -- 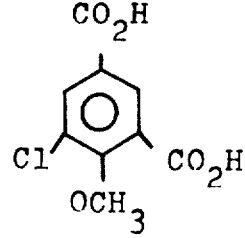 --.

Col. 9, line 29, change "carbons" to -- cartons --.

Col. 9, line 32, change "combined" to -- combed --.

Col. 14, Claim 11, line 44, insert -- Z -- before "is".

Col. 14, Claim 11, line 45, insert -- $Na^+$ -- after "$NH_4^+$, ".

Col. 14, Claim 14, line 64, change "$K^{30}$", to -- $K^+$ --.

Signed and Sealed this

*Twenty-fourth* Day of *April 1979*

[SEAL]

Attest:

RUTH C. MASON
*Attesting Officer*

DONALD W. BANNER
*Commissioner of Patents and Trademarks*